United States Patent
Kwon

(10) Patent No.: US 7,657,381 B2
(45) Date of Patent: Feb. 2, 2010

(54) METHOD OF DESIGNING PROBE SET, MICROARRAY HAVING SUBSTRATE ON WHICH PROBE DESIGNED BY THE METHOD IS IMMOBILIZED, AND COMPUTER READABLE MEDIUM ON WHICH PROGRAM FOR EXECUTING THE METHOD IS RECORDED

(75) Inventor: Tae-joon Kwon, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 506 days.

(21) Appl. No.: 11/226,082

(22) Filed: Sep. 14, 2005

(65) Prior Publication Data

US 2006/0058967 A1 Mar. 16, 2006

(30) Foreign Application Priority Data

Sep. 14, 2004 (KR) .................. 10-2004-0073366

(51) Int. Cl.
*G06F 7/00* (2006.01)
(52) U.S. Cl. .................. 702/19; 702/20; 703/11; 703/13; 707/102; 536/24.5; 435/6
(58) Field of Classification Search .................. None
See application file for complete search history.

(56) References Cited

U.S. PATENT DOCUMENTS

| 5,143,854 | A | 9/1992 | Pirrung et al. | 436/518 |
|---|---|---|---|---|
| 5,424,186 | A | 6/1995 | Fodor et al. | 435/6 |
| 5,445,934 | A | 8/1995 | Fodor et al. | 435/6 |
| 5,744,305 | A | 4/1998 | Fodor et al. | 435/6 |
| 7,288,371 | B1 * | 10/2007 | Bavykin et al. | 435/6 |
| 2002/0160401 | A1 * | 10/2002 | Nozaki et al. | 435/6 |
| 2003/0069701 | A1 | 4/2003 | Matsumoto et al. | 702/20 |
| 2004/0101845 | A1 | 5/2004 | Collins et al. | 435/6 |
| 2004/0157254 | A1 | 8/2004 | Kwon | 435/6 |

FOREIGN PATENT DOCUMENTS

| EP | 1 237 114 A2 | 9/2002 |
|---|---|---|
| JP | 2002-296279 A | 10/2002 |
| JP | 2002-330768 A | 11/2002 |
| JP | 2002-345480 A | 12/2002 |
| WO | WO 03/031654 A1 | 4/2003 |

OTHER PUBLICATIONS

"Detection and Identification of Mycobacterium Species Isolates by DNA Microarray"; Authors: Masao Fukushima, et al.; Journal of Clinical Microbiology; pp. 2605-2615 (2003).
European Search Report for Application No. 05019375.4-2405; Dated: Feb. 6, 2006.
Korean Intellectual Property Office, Notice to Submit Response w/English Translation dated: May 30, 2006.
Rouillard, JM et al., OligoArray: genome-scale oligonucleotide design for microarrays, Bioinformatics, vol. 18 No. 3, 2002, pp. 486-487.
Zhang, Z et al., Identification of characteristic oligonucleotides in the bacterial 16S ribosomal RNA sequence dataset, Bioinformatics, vol. 18 No. 2, 2002, pp. 244-250.
Borneman, J et al., Probe selection algorithms with applications in the analysis of microbial communities, Bioinformatics, vol. 17, Suppl. 1, 2001, pp. S39-S48.

* cited by examiner

*Primary Examiner*—Mary K Zeman
(74) *Attorney, Agent, or Firm*—Cantor Colburn LLP

(57) ABSTRACT

A method of designing a probe set for identifying a target sequence from a plurality of target sequence groups by a hybridization reaction is provided. The method includes: (a) selecting a first target sequence group including a plurality of target sequences; (b) selecting oligonucleotides specifically binding to the target sequences from the first target sequence group as a probe; (c) selecting one or more target sequences having no specifically binding probe from the first target sequence group as a second target sequence group; (d) selecting oligonucleotides specifically binding to the target sequences from the second target sequence group as a probe, wherein the operations (c) and (d) are repeated until a target sequence having no specifically binding probe is absent in the second target sequence group.

4 Claims, 4 Drawing Sheets

FIG. 3

|  | PROBE a | PROBE b | PROBE c | PROBE d |
|---|---|---|---|---|
| TARGET DNA A | O | X | O | X |
| TARGET DNA B | X | O | X | O |
| TARGET DNA C | X | X | O | O |
| TARGET DNA D | X | X | X | O |

FIG. 5

```
              ***************  *****  **********  ****   ****  ******
AJ536040.1 ATGCTACAATGGCCGGTACAAAGGGCTGCGATGCCGTGAGGTTTAGCGAA (SEQ ID NO.1)
AJ536033.1 ATGCTACAATGGCCGGTACAAAGGGCTGCGATGCCGTGAGGTTAAGCGAA (SEQ ID NO.2)
AJ536033.1 ATGCTACAATGGCCGGTACAAAGGGCTGCGATGCCGTAAGGTTAAGCGAA (SEQ ID NO.3)
AJ536033.1 ATGCTACAATGGCCGGTACAAAGGGCTGCGATGCCGCAAGGTTAAGCGAA (SEQ ID NO.4)
AJ536031.1 ATGCTACAATGGCCGGTACAAAGGGCTGCGATGCCGCGAGGTTAAGCGAA (SEQ ID NO.5)
AJ536039.1 ATGCTACAATGGCCGGTACAAAGGGCTGCGATGCCGTGAGGTGGAGCGAA (SEQ ID NO.6)
AJ536038.1 ATGCTACAATGGCCAGTACAGAGGGCTGCGAAGCCGTAAGGTGGAGCGAA (SEQ ID NO.7)
```

METHOD OF DESIGNING PROBE SET, MICROARRAY HAVING SUBSTRATE ON WHICH PROBE DESIGNED BY THE METHOD IS IMMOBILIZED, AND COMPUTER READABLE MEDIUM ON WHICH PROGRAM FOR EXECUTING THE METHOD IS RECORDED

CROSS-REFERENCE TO RELATED PATENT APPLICATION

This application claims the benefit of Korean Patent Application No. 10-2004-0073366, filed on Sep. 14, 2004, in the Korean Intellectual Property Office, the disclosure of which is incorporated herein in its entirety by reference.

BACKGROUND OF THE INVENTION

1. Field of the Invention

The present invention relates to a method of designing a probe set for identifying a specific target sequence group by a hybridization reaction, a microarray having a substrate on which a probe designed by the method is immobilized, and a computer readable medium on which a program for executing the method is recorded.

2. Description of the Related Art

A polynucleotide microarray is a microarray having a substrate on which a polynucleotide group is immobilized with high density. The polynucleotide group is immobilized on a prescribed area of the substrate. Examples of polynucleotide microarrays are disclosed in U.S. Pat. Nos. 5,445,934 and 5,744,305.

Generally, a photolithography method has been used to manufacture a polynucleotide microarray. In this method, a polynucleotide array is manufactured by repeatedly exposing prescribed areas of a substrate where monomers protected by a removable group have been applied to energy source to remove the protective group, and repeatedly coupling the monomers protected by the removable group. Thus, polynucleotides immobilized on a polynucleotide microarray are synthesized by extending monomers one-by-one.

On the other hand, in the case of using a spotting method, a microarray is formed by immobilizing previously synthesized polynucleotides on prescribed areas. Methods of manufacturing such a polynucleotide microarray are disclosed in U.S. Pat. Nos. 5,744,305, 5,143,854, and 5,424,186, disclosures of which are included herein by reference.

Polynucleotides (referred to as a probe, a nucleic acid probe, or a polynucleotide probe) immobilized on a microarray are used to detect or identify target sequences due to the ability to hybridize to target sequences. With respect to conventional DNA probes, a standard condition for selecting a DNA probe for a target sequence is set up, and then a DNA sequence meeting the standard conditions is selected. The standard conditions or others for the selected DNA sequence are inspected to select the most preferable probe sequence. The standard conditions may include a length of a probe, Tm of a probe (the temperature at which 50% of double stranded DNA molecules are dissociated into two single stranded DNAs), a threshold value of the sequence homology with other sequences, and the like. After a candidate DNA probe meeting the standard conditions has been selected, the candidate DNA probe is examined with regard to Tm and sequence homology to determine whether or not the candidate DNA probe is unique only to a target sequence and whether or not the candidate DNA probe is a sequence that can easily induce cross hybridization. As a result, the most preferable probe among the candidate DNA probes meeting the standard conditions is selected as a sequence specifically binding to a target DNA sequence. However, in such a method of designing a probe, since a specific sequence hybridizing only to each target sequence with no cross hybridization to other sequences is selected as a probe, it is difficult to design a specific probe when sequence homology between target sequences is high.

There have been several attempts to solve the above-described problem. For example, US Patent Publication No. 2003/0069701 discloses a biochip having a substrate on which a plurality of probes for one target sequence is spotted. This disclosure relates to a method of providing additional information on a target sequence by the combination of previously inspected probes. However, the method cannot be used to design by identifying target sequences. US Patent Publication No. 2002/0160401 also discloses a biochip having a substrate on which a plurality of probes is spotted for one target sequence. This disclosure relates to a method of using information on a common probe as additional information, and a method of identifying a target sequence to design a unique probe is not disclosed.

Therefore, a method of designing a probe for identifying a target sequence from a plurality of target sequence groups by a hybridization reaction and then estimating a target sequence by the relationship between the designed probes still is required.

SUMMARY OF THE INVENTION

The present invention provides a method of efficiently designing a probe set for identifying a target sequence from a target sequence group including a plurality of target sequences groups by a hybridization reaction.

The present invention also provides a microarray having a substrate on which a probe designed by the method is immobilized.

The present invention also provides a computer readable medium on which a program for executing the method is recorded.

According to the present invention, there is provided a method of designing a probe set for identifying a target sequence from a plurality of target sequence groups by hybridization, comprising: (a) selecting a first target sequence group including a plurality of target sequences; (b) selecting oligonucleotides specifically binding to the target sequences from the first target sequence group as a probe; (c) selecting one or more target sequences having no specifically binding probe from the first target sequence group as a second target sequence group; (d) selecting oligonucleotides specifically binding to the target sequences from the second target sequence group as a probe, wherein the operations (c) and (d) are repeated until a target sequence having no specifically binding probe is absent in the second target sequence group.

According to the present invention, a first target sequence group including a plurality of target sequences is selected. In the method of the present invention, "target sequence" means a polynucleotide to be identified by the combination with a probe. A target sequence includes genomic DNA, DNA fragments digested with a restriction enzyme, PCR products, and the like. In general, genomic DNA fragments obtained by amplifying specific regions in genomic DNA by PCR are often used. The method of the present invention is a method of designing a probe set in the case where a plurality of target sequences are available.

Next, oligonucleotides specifically binding to target sequences from the first target sequence group are selected as a probe. Here, "specifically binding probe" means a probe specifically binding to one target sequence in the first target sequence group but not binding to the other target sequences in the first target sequence group. Preferably, the specifically binding probe is a partial sequence or the corresponding complementary sequence which is included in one target sequence in the first target sequence group but is not included in the other target sequences in the first target sequence group. In the case of using the specifically binding probe, regardless the presence or absence of any other DNA, when a signal is observed from this probe, it is possible to evaluate the DNA as being mixed. However, when a signal is not observed form this probe, it is possible to evaluate the DNA as not being mixed.

In the present invention, the selection of a probe may be performed according to conventionally known methods. With respect to a conventional DNA probe, standard conditions for the selection of a DNA probe for a target sequence are set up, and then a DNA sequence meeting the standard conditions is selected. The standard conditions or others are inspected for the selected DNA sequence to select the most preferable probe sequence. The standard conditions may include a length of a probe, Tm of a probe (the temperature at which double stranded DNA is dissociated into two single stranded DNA), a threshold value of the sequence homology with other DNA's, and the like. When a candidate DNA probe meeting the standard conditions is selected, the candidate DNA probe is examined by Tm and sequence homology to determine whether or not the candidate DNA probe is unique to a target sequence and whether or not the candidate DNA probe is a sequence that can easily induce cross hybridization. As a result, the most preferable probe among the candidate DNA probes meeting the standard conditions is selected as a sequence specifically binding to a target DNA sequence. If the DNA probe is one capable of specifically binding to a target sequence, two or more DNA probes may be selected for one target DNA.

In the method of the present invention, a second target sequence group including target sequences having no specifically binding probe as described above is selected. Next, a DNA probe specifically binding to the target sequence is selected from the second target sequence group through the same process as described in the process of specifically selecting a probe from the first target sequence group. The above-described processes may be repeated until a target sequence having no specifically binding probe is absent in the second target sequence group. In repeating the processes described above, there can be a case where it is impossible to select a specific probe from the second target sequence group selected according to the selection conditions of DNA probe. This case may occur, for instance, when sequence homology between target sequences included in the second target sequence is very high. Accordingly, in an embodiment of the present invention, the processes of selecting a second target sequence group and then selecting a probe specifically binding to a target sequence from the second target sequence group are repeated until a target sequence capable of selecting a specific probe is no more present. In this case, the probe selected is a sequence present in common in the sequence group having high sequence homology or its complementary sequence, and may be a sequence absent in the other target sequences in the target sequence group or its complementary sequence.

A plurality of probes obtained from these processes is selected as a probe set for identifying the first target sequence group by a hybridization reaction. Such a probe set can be immobilized on the substrate of a microarray. In the present invention, the immobilization of DNA probes on the substrate can be performed according to a method well known in the prior art. For example, the surface of a substrate is activated by compounds having an amino group, and then the DNA probes may be immobilized by coupling the 5' end and 3' end of the DNA probes activated by compounds such as carbodiimide. Those skilled in the art can manufacture a DNA probe microarray on which the DNA probes of the present invention are immobilized by properly adjusting a conventionally known method for immobilization. In the present invention, "immobilization" includes the immobilization of the probe set of the present invention on a substrate by spotting, and in addition, the immobilization by synthesizing the probe sequence one-by-one on a substrate by using photolithography.

Accordingly, the present invention also provides a polynucleotide microarray having a substrate on which the probe set designed by the method of the present invention is immobilized.

The present invention also provides a computer readable medium on which a program for executing the method of the present invention is recorded.

The present invention may be embodied in the form of a computer readable code in a computer readable recording medium (including all devices having an information processing function). The computer readable recording medium includes any kind of recording media to store computer readable data such as read-only memory (ROM), random-access memory (RAM), CD-ROMs, magnetic tape, floppy disk, optical data storage device and the like.

BRIEF DESCRIPTION OF THE DRAWINGS

The above and other features and advantages of the present invention will become more apparent by describing in detail exemplary embodiments thereof with reference to the attached drawings in which:

FIG. 3 illustrates a method of adding a mixture of unknown target sequences to a microarray to carry out a hybridization reaction according to an embodiment of the present invention, the microarray having a substrate on which probes a, b, c, and d are immobilized, the probes being selected as a probe set for the first target sequence group (A, B, C, and D) according to FIG. 1 and FIG. 2 to identify the type of the target sequences in the mixture from the obtained signals;

FIG. 5 illustrates target sequences in seven species of *Mycobacterium* and probe sequences designed from the target sequences.

DETAILED DESCRIPTION OF THE INVENTION

Figure 1:
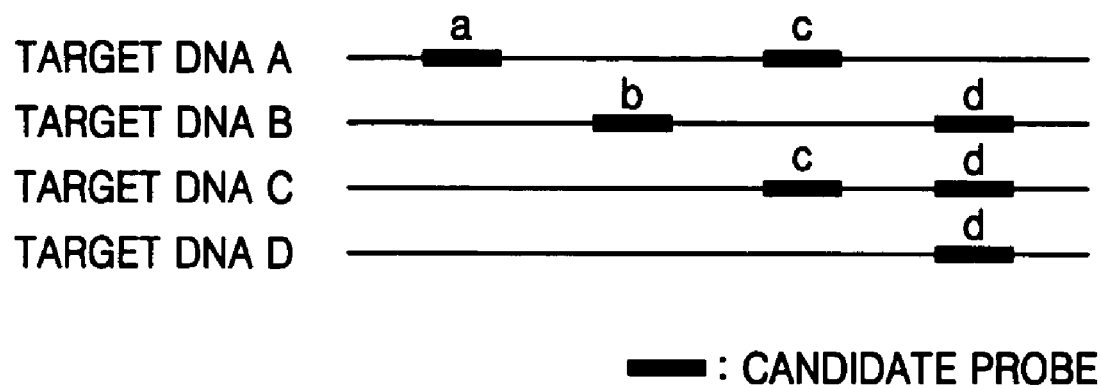
FIG. 1 schematically illustrates candidate probes selected from a first target sequence group including A, B, C, and D according to the conditions of probe selection.

Hereinafter, a method of designing a probe according to an embodiment of the present invention will be described in more detail with reference to the accompanying drawings. FIG. 1 schematically illustrates candidate probes selected from a first target sequence group including A, B, C, and D according to the conditions of probe selection. The first target sequence group including four target sequences (A, B, C, and D) is selected, and then candidate DNA probes (a, b, c, and d) are determined with reference to these target sequences. Candidate DNA probes specific to each target sequence are selected from these candidate DNA probes. In FIG. 1, probe "a" is selected as a DNA probe specifically binding to A of four target sequences. Probe "a" has no sequence which is homologous and complementary to the other target sequences B, C, and D among the first target sequence group. Similarly, probe "b" is selected as a DNA probe capable of specifically binding to B of the first target sequence group. On the other hand, the candidate probes "c" and "d" for the target sequences C and D cannot be selected as specific probes since a sequence homologous to the target sequences A and B is present therein. The target sequences C and D having no specific probe are selected as a second target sequence group.

Figure 2:
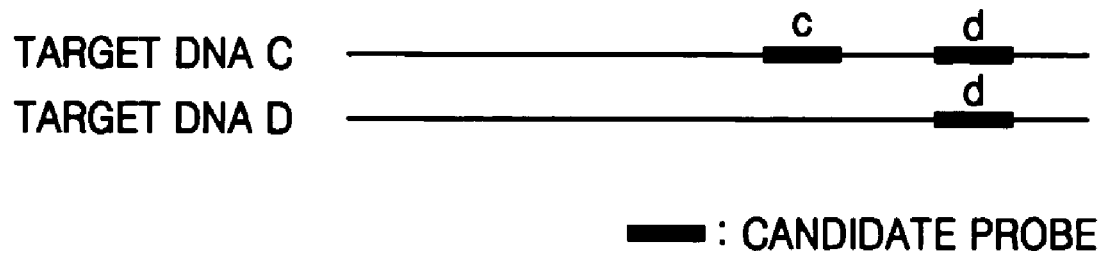
FIG. 2 schematically illustrates specific candidate DNA probes present in a second target sequence group.

FIG. 2 schematically illustrates specific candidate DNA probes present in the second target sequence group. The second target sequence group includes the target sequences C and D having no specific probe in the process of selecting a specifically binding probe from the first target sequence group. Candidate DNA probes (c and d) are determined with reference to nucleotide sequences of the second target sequence group. Candidate DNA probes specific to target sequences are selected from the candidate DNA probes. In FIG. 2, a probe "c" is selected as a DNA probe capable of specifically binding to C of the two target sequences. The probe "c" has no sequence which is homologous and complementary to the other target sequence D among the second target sequence group. On the other hand, the candidate probe "d" for target sequence D cannot be selected as a specific probe since a sequence homologous to the target sequence C is present therein. The target sequence D having no specific probe is selected as another second target sequence group. The processes of probe selection as described above are repeated to select the probe "d" as a specific probe. Accordingly, the probes a, b, c, and d are selected as a probe set for identifying the first target sequence group (A, B, C, and D) by hybridization reaction.

Figure 4:
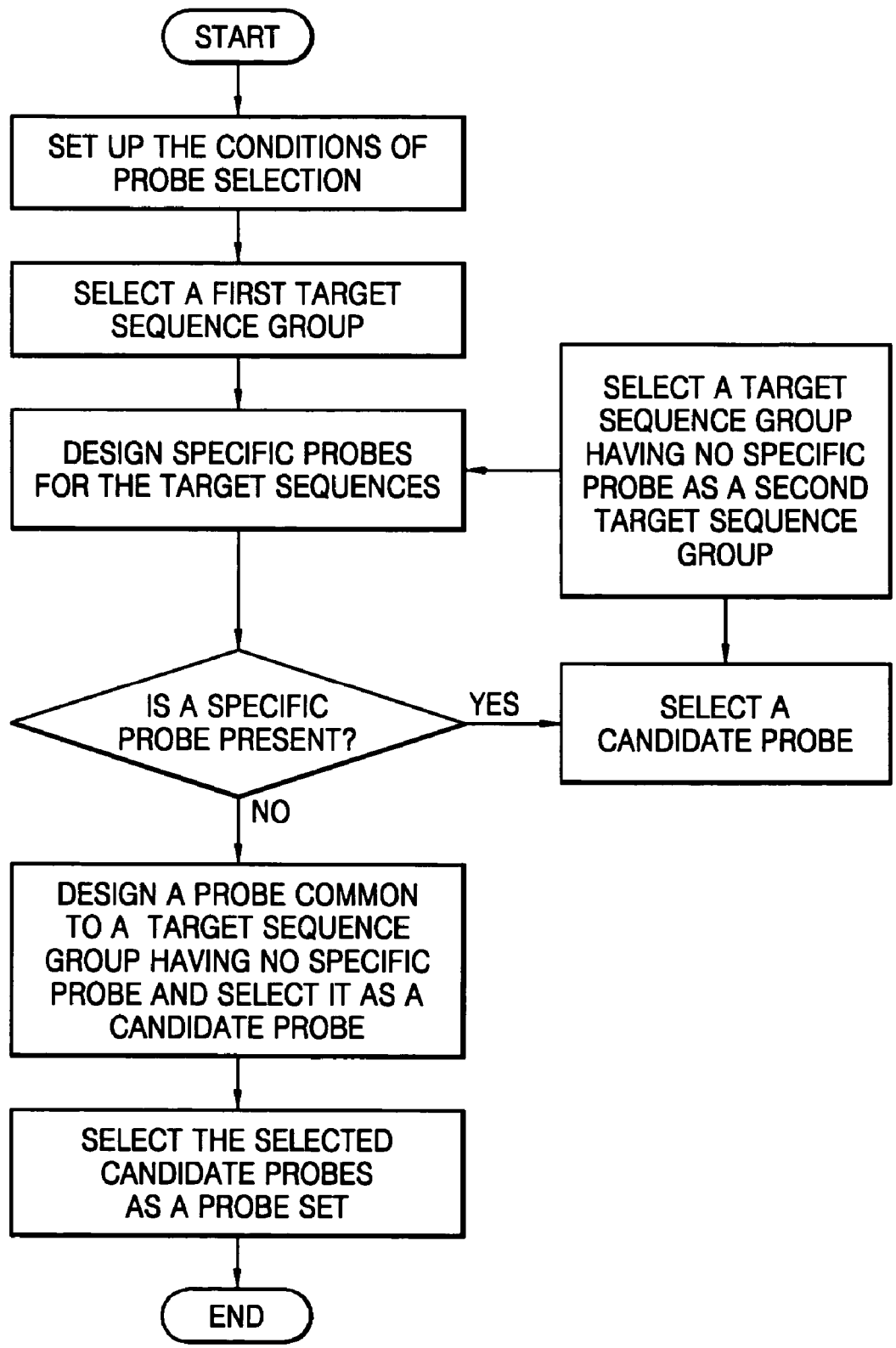
FIG. 4 is a flow chart illustrating a method of designing a probe according to an embodiment of the present invention.

FIG. 3 illustrates a method of adding a mixture of unknown target sequences to a microarray to carry out hybridization reaction according to an embodiment of the present invention, the microarray having a substrate on which probes a, b, c, and d are immobilized, the probes being selected as a probe set for the first target sequence group (A, B, C, and D) according to FIG. 1 and FIG. 2 to identify the type of the target sequences in the mixture from the signals obtained by the hybridization reaction. For example, if the target sequence A is present, signals are observed at the spots of the probes "a" and "b", and if the target sequence B is present, signals are observed at the spots of the probes "b" and "d". If the target sequence C is present, signals are observed at the spots of the probes "c" and "d", and if the target sequence D is present, a signal is observed at the spot of the probe "d". The signal at the spot of the probe "d" can be observed from all of the target sequences A, C, and D. However, these target sequences can be classified by the interrelation between the spots of the probes FIG. 4 is a flow chart illustrating a method of designing a probe according to an embodiment of the present invention. First, according to FIG. 4, the conditions of probe selection are set up, and then a target sequence group including a plurality of target sequences is selected in accordance with the conditions. Subsequently, specific probes for the target sequences are designed. As the result of the probe design, if a specific probe is present, this specific probe is selected as a candidate, and target sequences having no specific probe are selected as a second target sequence group. The process of designing specific probes for the target sequences is repeated with respect to the second sequence group. When it is judged impossible to design a specific probe for the second target sequence group, a probe common to the target sequence group having no specific probe is designed and simultaneously, previously selected candidate probes are put together for selection as a final probe set.

Hereinafter, the present invention will be described in more detail with reference to the following example, and the scope of the present invention is, however, not limited to this example.

Example 1

Design of Probe Set Capable of Identifying Seven Species of *Mycobacterium*

In this example, there was designed a probe set available to identify the bacterial species from a part of regions of 16S rRNA derived from seven species of *Mycobacterium* according to the method of the present invention.

In this example, the process of identifying Tm or sequence homology is omitted, and the process of designing a unique probe will be exemplified in more detail.

TABLE 1

| Target Species and Target Sequence Regions | |
|---|---|
| Species | Sequence |
| AJ536040.1 | SEQ ID NO. 1 |
| AJ536033.1 | SEQ ID NO. 2 |
| AJ536037.1 | SEQ ID NO. 3 |
| AJ536036.1 | SEQ ID NO. 4 |
| AJ536031.0 | SEQ ID NO. 5 |
| AJ536039.1 | SEQ ID NO. 6 |
| AJ536038.1 | SEQ ID NO. 7 |

Probes of five base pairs designed based on the information on these target sequence regions are shown in FIG. 5. FIG. 5 shows target sequences in seven species of *Mycobacterium* and probe sequences designed from the target sequences. In FIG. 5, '*' means a consensus sequence.

First, the unique probe of sequence 5'-GTTTA-3' (4145) was designed for AJ536040.1 (a numeral in parentheses indicates the position in the target sequence). In addition, there were designed the unique probe of sequence 5'-CCAGT-3' (13-17) for AJ536038.1, the unique probe of sequence 5'-GCMG-3' (36-40) for AJ536036.1, and the unique probe of sequence 5'-GCGAG-3' (36-40) for AJ536031.1. Next, since there is no probe capable of designing a unique probe, a primary second target sequence group includes three target sequences except the four target sequences.

The unique probe of sequence 5'-GTGGA-3' (41-45) was designed for AJ536039.1 from among the primary second target sequence group. The unique probe for AJ536039.1 is not a unique probe when it is compared on a level with AJ536038.1. But, since AJ536038.1 had a unique probe in the previous operation to be excluded from the target sequence group, the unique probe of sequence 5'-GTGGA-3' can be considered to be a unique probe for AJ536039.1. Similarly, the probe of sequence 5'-GTAAG-3' (36-40) can be designed for AJ536037.1. A secondary second target sequence group includes 1 target sequence not capable of designing a unique probe.

The probe of sequence 5'-GTGAG-3' (36-40) was designed as the unique probe for AJ536033.1 of the secondary target sequence group. All of the probes designed as described above were selected as one probe set for identifying the seven species of *Mycobacterium*. One example of the method of identifying target sequences using the designed probe set is as follows.

TABLE 2

| Probe\species | AJ536040 | AJ536033 | AJ536037 | AJ536036 | AJ536031 | AJ536039 | AJ536038 |
|---|---|---|---|---|---|---|---|
| GTTTA | O | | | | | | |
| CCAGT | | | | | | | O |
| GCAAG | | | | O | | | |
| GCGAG | | | | | O | | |
| GTGGA | | | | | | O | O |
| GTAAG | | | O | | | | O |
| GTGAG | O | O | | | | O | |

According to the method of the present invention, it is possible to rapidly and easily design a DNA probe efficiently to identify a specific target sequence group by a hybridization reaction.

A microarray according to the present invention can be used to identify a target sequence in a specific target sequence group.

A computer readable medium according to the present invention can be efficiently used to design a DNA probe for identifying a specific target sequence group by a hybridization reaction.

What is claimed is:

1. A method of designing a probe set for identifying a target sequence from a plurality of target sequences by hybridization, comprising:

on a specifically programmed computer,
(a) selecting a first target sequence group consisting of a plurality of target sequences;
(b) selecting an oligonucleotide sequence specifically binding to a target sequence from the first target sequence group as a probe sequence, wherein the oligonucleotide sequence does not cross hybridize with other target sequences in the first target sequence group;
(c) selecting the target sequences having no specifically binding probe sequence from the first target sequence group as a second target sequence group;
(d) selecting an oligonucleotide sequence specifically binding to a target sequence from the second target sequence group as a probe sequence, wherein the oligonucleotide sequence does not cross hybridize with other target sequences in the second target sequence group;
(e) repeating operations (c) and (d) until each target sequence in the plurality of target sequences has a specifically binding probe sequence or until it is impossible to select a specifically binding probe sequence for each target sequence in the plurality because of high sequence homology among a subset of the target sequences in the plurality, and
wherein when it is impossible to select a specifically binding probe sequence for each target sequence in the plurality because of high sequence homology among a subset of the target sequences, a sequence present in common in the subset, but not present in the other target sequences of the plurality, or the complementary sequence thereof, is selected as a probe sequence; and
(f) displaying the selected probe sequences to a user.

2. A computer readable medium on which a program is recorded for executing a method, the method comprising
(a) selecting a first target sequence group consisting of a plurality of target sequences;
(b) selecting an oligonucleotide sequence specifically binding to a target sequence from the first target sequence group as a probe sequence, wherein the oligonucleotide sequence does not cross hybridize with other target sequences in the first target sequence group;
(c) selecting the target sequences having no specifically binding probe sequence from the first target sequence group as a second target sequence group;
(d) selecting an oligonucleotide sequence specifically binding to a target sequence from the second target sequence group as a probe sequence, wherein the oligonucleotide sequence does not cross hybridize with other target sequences in the second target sequence group;
(e) repeating operations (c) and (d) until each target sequence in the plurality of target sequences has a specifically binding probe sequence or until it is impossible to select a specifically binding probe sequence for each target sequence in the plurality because of high sequence homology among a subset of the target sequences in the plurality, and wherein when it is impossible to select a specifically binding probe sequence for each target sequence in the plurality because of high sequence homology among a subset of the target sequences, a sequence present in common in the subset target sequences, but not present in the other target sequences of the plurality, or the complementary sequence thereof, is selected as a probe sequence; and displaying the selected probe sequences to a users, wherein the computer readable medium is a device to store computer readable data.

3. The method according to claim 1, further comprising immobilizing probes consisting of the selected probe sequences on a substrate to obtain a micro array.

4. The computer readable medium of claim 2, wherein the device consists of a read-only memory (ROM), a random-access memory (RANT), a CD-ROM, a magnetic tape, a floppy disk, or an optical data storage device.

* * * * *

SEQUENCE LISTING

<160> NUMBER OF SEQ ID NOS: 7

<210> SEQ ID NO 1
<211> LENGTH: 50
<212> TYPE: DNA
<213> ORGANISM: Artificial Sequence
<220> FEATURE:
<223> OTHER INFORMATION: A target nucleotide sequence

<400> SEQUENCE: 1
atgctacaat ggccggtaca aagggctgcg atgccgtgag gtttagcgaa         50

<210> SEQ ID NO 2
<211> LENGTH: 50
<212> TYPE: DNA
<213> ORGANISM: Artificial Sequence
<220> FEATURE:
<223> OTHER INFORMATION: A target nucleotide sequence

<400> SEQUENCE: 2
atgctacaat ggccggtaca aagggctgcg atgccgtgag gttaagcgaa         50

<210> SEQ ID NO 3
<211> LENGTH: 50
<212> TYPE: DNA
<213> ORGANISM: Artificial Sequence
<220> FEATURE:
<223> OTHER INFORMATION: A target nucleotide sequence

<400> SEQUENCE: 3
atgctacaat ggccggtaca aagggctgcg atgccgtaag gttaagcgaa         50

<210> SEQ ID NO 4
<211> LENGTH: 50
<212> TYPE: DNA
<213> ORGANISM: Artificial Sequence
<220> FEATURE:
<223> OTHER INFORMATION: A target nucleotide sequence -continued

```
<400> SEQUENCE: 4
atgctacaat ggccggtaca aagggctgcg atgccgcaag gttaagcgaa            50

<210> SEQ ID NO 5
<211> LENGTH: 50
<212> TYPE: DNA
<213> ORGANISM: Artificial Sequence
<220> FEATURE:
<223> OTHER INFORMATION: A target nucleotide sequence

<400> SEQUENCE: 5
atgctacaat ggccggtaca aagggctgcg atgccgcgag gttaagcgaa            50

<210> SEQ ID NO 6
<211> LENGTH: 50
<212> TYPE: DNA
<213> ORGANISM: Artificial Sequence
<220> FEATURE:
<223> OTHER INFORMATION: A target nucleotide sequence

<400> SEQUENCE: 6
atgctacaat ggccggtaca aagggctgcg atgccgtgag gtggagcgaa            50

<210> SEQ ID NO 7
<211> LENGTH: 50
<212> TYPE: DNA
<213> ORGANISM: Artificial Sequence
<220> FEATURE:
<223> OTHER INFORMATION: A target nucleotide sequence

<400> SEQUENCE: 7
atgctacaat ggccagtaca gagggctgcg aagccgtaag gtggagcgaa            50
```